United States Patent
Katoh et al.

(10) Patent No.: US 8,652,364 B2
(45) Date of Patent: *Feb. 18, 2014

(54) POLYMER FILM, ULTRAVIOLET ABSORBER, MEROCYANINE COMPOUND AND PROCESS FOR PREPARING MEROCYANINE COMPOUND

(75) Inventors: Shunya Katoh, Minami-ashigara (JP); Hiroko Kamee, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/046,353

(22) Filed: Mar. 11, 2011

(65) Prior Publication Data

US 2011/0220843 A1    Sep. 15, 2011

(30) Foreign Application Priority Data

Mar. 11, 2010 (JP) .................................. 2010-054065

(51) Int. Cl.
| | |
|---|---|
| *F21V 9/06* | (2006.01) |
| *C07D 239/24* | (2006.01) |
| *C07D 231/08* | (2006.01) |
| *C07D 231/10* | (2006.01) |
| *C07D 327/04* | (2006.01) |
| *C07D 319/06* | (2006.01) |

(52) U.S. Cl.
USPC ......... 252/589; 428/1.1; 544/301; 548/366.7; 549/40; 549/65; 549/67; 549/274

(58) Field of Classification Search
USPC ................... 428/1.1; 252/299.01, 299.5, 589; 544/298, 304, 335, 301; 546/246; 549/274, 40, 65, 67; 548/366.7
See application file for complete search history.

(56) References Cited

U.S. PATENT DOCUMENTS

| | | | |
|---|---|---|---|
| 4,195,999 A * | 4/1980 | Adachi et al. ................ | 430/507 |
| 8,178,601 B2 | 5/2012 | Fukagawa et al. | |
| 2001/0039195 A1 * | 11/2001 | Nickum ........................ | 455/557 |
| 2009/0080074 A1 * | 3/2009 | Fukagawa et al. ............ | 359/500 |
| 2010/0323285 A1 * | 12/2010 | Einaga ............................. | 430/7 |
| 2011/0229662 A1 * | 9/2011 | Kamee et al. .................. | 428/1.3 |
| 2012/0140161 A1 * | 6/2012 | Nimura et al. ................ | 349/194 |

FOREIGN PATENT DOCUMENTS

| | | | |
|---|---|---|---|
| JP | 53-128333 A | | 11/1978 |
| JP | 08-239509 A | | 9/1996 |
| JP | 2001324807 A | * | 11/2001 |
| JP | 2003-277349 A | | 10/2003 |
| JP | 2009-064006 A | | 3/2009 |
| JP | 2009-064007 A | | 3/2009 |
| JP | 2009-067973 A | | 4/2009 |
| JP | 2009-079213 A | | 4/2009 |
| JP | 2009-270062 A | | 11/2009 |

OTHER PUBLICATIONS

CAPLUS 2001: 847635.*
Office Action dated Nov. 5, 2013 on Japanese Patent Application No. 2010-054065.

* cited by examiner

*Primary Examiner* — Shean C Wu
(74) *Attorney, Agent, or Firm* — Sughrue Mion, PLLC

(57) ABSTRACT

A polymer film comprising at least one compound represented by formula (I) is disclosed. $A^1$ and $A^2$ each independently represent a group having a Hammett's σp value of 0.2 or more, or bond each other to form a cyclic active methylene structure; and $X^1$ and $X^2$ each independently represent a hydrogen atom, aryl group, hetero-cyclic group, cyano, N-alkyl- or N-aryl-carbamoyl, or alkyl- or aryl-oxycarbonyl, or bond each other to form a saturated ring in which nitrogen and carbon atoms are embedded, and the group and ring may have at least one substituent.

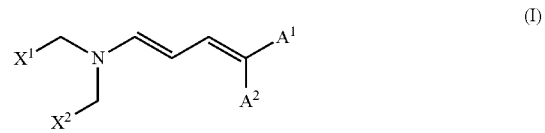

(I)

7 Claims, No Drawings

POLYMER FILM, ULTRAVIOLET ABSORBER, MEROCYANINE COMPOUND AND PROCESS FOR PREPARING MEROCYANINE COMPOUND

CROSS-REFERENCE TO RELATED APPLICATIONS

The present application claims the benefit of priority from Japanese Patent Application No. 2010-054065, filed on Mar. 11, 2010, the contents of which are herein incorporated by reference in their entirety.

BACKGROUND OF THE INVENTION

1. Field of the Invention

The present invention relates to a light resistant polymer film, to an ultraviolet absorber and a merocyanine compound useful for preparing the polymer film or the like, and to a novel process for preparing merocyanine compounds.

2. Background Art

For attaining ultraviolet absorption ability, adding an ultraviolet absorber to a polymer film such as a protective film has been known. For example, the polymer film containing a merocyanine compound as an ultraviolet absorber is disclosed in JP-A-8-239509. And, in JP-A-2009-67973, there has been proposed a polymer material containing, as an ultraviolet-absorbing agent, a merocyanine compound, and also proposed a molded article, coated-ultraviolet absorbing layer or the like prepared by using the polymer material. And in JP-A-2009-64006 and JP-A-2009-64007, using a merocyanine compound as a wavelength-dispersing agent for polymer films has been also proposed.

On the other hand, conventional merocyanine-series ultraviolet absorbers don't have sufficient light-fastness, and it is known that their ultraviolet-absorbing abilities decrease over time. For example, in JP-A-2009-270062, for improving light-fastness, using another ultraviolet absorber along with the merocyanine-series ultraviolet absorber has been proposed.

The process for preparing the mecrocyanine compound is disclosed in JP-A-2003-277349.

SUMMARY OF THE INVENTION

One object of the invention is to provide an ultraviolet-absorbable polymer film and a merocyanine-series ultraviolet absorber, having high light-fastness.

Another object of the invention is to provide novel merocyanine compounds useful in various usages such as an ultraviolet absorber, and a process for preparing them.

The means for achieving the objects are as follows.

[1] A polymer film comprising at least one compound represented by formula (I):

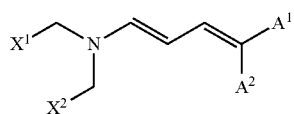

wherein $A^1$ and $A^2$ each independently represent a group having a Hammett's σp value of 0.2 or more, or bond each other to form a cyclic active methylene structure; and $X^1$ and $X^2$ each independently represent a hydrogen atom, aryl group, hetero-cyclic group, cyano, N-alkyl- or N-aryl-carbamoyl, or alkyl- or aryl-oxycarbonyl, or bond each other to form a saturated ring in which nitrogen and carbon atoms are embedded, and the group and ring may have at least one substituent.

[2] The polymer film of [1], wherein, in formula (I), $A^1$ and $A^2$ each independently represent an alkyl- or aryl-carbonyl group, alkyl- or aryl-oxycarbonyl group, N-alkyl- or N-aryl-carbamoyl, or cyano, which may have at least one substituent, or bond each other to form a ring selected from Active Methylene Group (II):

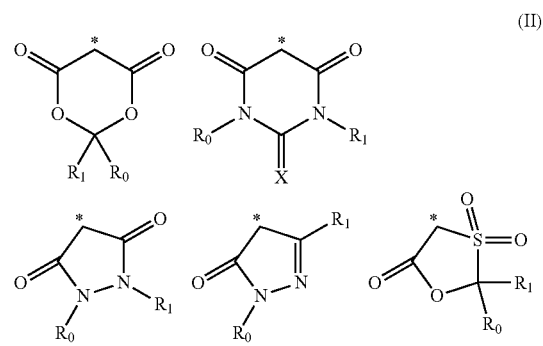

where, in formulas, "*" indicates a portion linking to formula (I); $R^0$ and $R^1$ each independently represent a hydrogen atom or an alkyl or phenyl group which may have at least one substituent, or bond each other to form a ring; and X represents an oxygen or sulfur atom.

[3] The polymer film of [1] or [2], wherein, in formula (I), $A^1$ and $A^2$ represent cyano, or bond each other to form a ring selected from the above-described Active Methylene Group (II).

[4] The polymer film of any one of [1]-[3], wherein, in formula (I), $X^1$ and $X^2$ each independently represent an aryl group, alkyl- or aryl-oxycarbonyl or cyano, or bond each other to form a saturated ring in which nitrogen and carbon atoms are embedded.

[5] The polymer film of [1], wherein said at least one compound is a compound represented by formula (III):

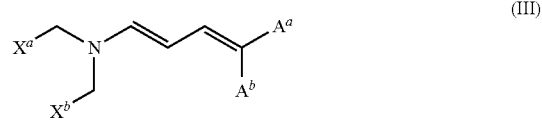

wherein $X^a$ and $X^b$ each independently represent cyano or an alkyl- or aryl-oxycarbonyl, which may have at least one substituent; and $A^a$ and $A^b$ each independently represent a group having a Hammett's σp value of 0.2 or more, or bond each other to form a cyclic active methylene structure.

[6] The polymer film of [5], wherein in formula (III), $A^a$ and $A^b$ each independently represent an alkyl- or aryl-carbonyl group, alkyl- or aryl-oxycarbonyl group, alkyl- or aryl-sulfonyl group, N-alkyl- or N-aryl-carbamoyl, or cyano, which may have at least one substituent, or bond each other to form a ring selected from the above-described Active Methylene Group (II).

[7] The polymer film of [1], wherein said at least one compound is a compound represented by formula (IV):

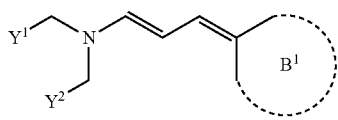
(IV)

wherein $Y^1$ and $Y^2$ each independently represent an aryl group which may have at least one substituent, or bond each other to from a saturated ring in which nitrogen and carbon atoms are embedded; and $B^1$ represents a cyclic active methylene structure.

[8] The polymer film of [7], wherein, in formula (IV), $B^1$ is one selected from the above-described Active Methylene Group (II).

[9] The polymer film of [7] or [8], wherein, in formula (IV), $Y^1$ and $Y^2$ each independently represent an aryl group which may have at least one substituent.

[10] The polymer film of [1], wherein said at least one compound is a compound represented by formula (V) or (VII):

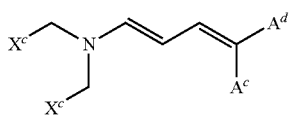
(V)

wherein $X^c$ represents cyano or an alkyl-oxycarbonyl; and $A^c$ and $A^d$ each independently represent an alkyl- or aryl-carbonyl group, alkyl-oxycarbonyl group or cyano, or bond each other to form a cyclic group selected from the above-described Active Methylene Group (II):

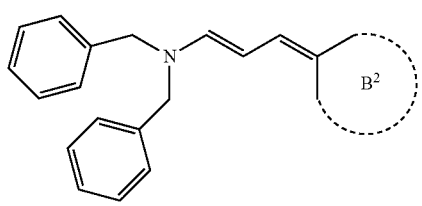
(VII)

where, in formula, $B^2$ represents a cyclic group selected from the above-described Active Methylene Group (II).

[11] The polymer film of [10], wherein the compound represented by formula (V) is a compound represented by formula (VI):

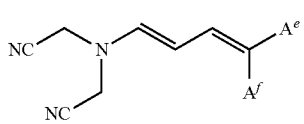
(VI)

where, in formula (VI), $A^e$ and $A^f$ each independently represent an alkyl- or aryl-carbonyl group, alkyl-oxycarbonyl group, or cyano, or bond each other to form a cyclic group selected from the above-described Active Methylene Group (II).

[12] A retardation film comprising a polymer of any one of [1]-[11], and an optically anisotropic layer of a cured liquid crystal composition.

[13] An ultraviolet absorber comprising at least one compound represented by formula (III):

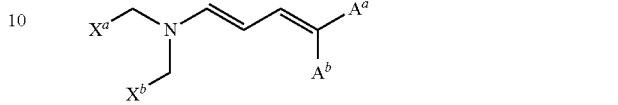
(III)

wherein $X^a$ and $X^b$ each independently represent cyano or an alkyl- or aryl-oxycarbonyl, which may have at least one substituent; and $A^a$ and $A^b$ each independently represent a group having a Hammett's σp value of 0.2 or more, or bond each other to form a cyclic active methylene structure.

[14] The ultraviolet absorber [13], wherein in formula (III), $A^a$ and $A^b$ each independently represent an alkyl- or aryl-carbonyl group, alkyl- or aryl-oxycarbonyl group, alkyl- or aryl-sulfonyl group, N-alkyl- or N-aryl-carbamoyl, or cyano, which may have at least one substituent, or bond each other to form a ring selected from the above-described Active Methylene Group (II).

[15] An ultraviolet absorber comprising at least one compound represented by formula (IV):

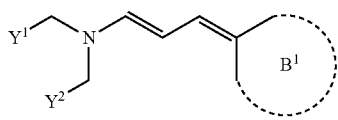
(IV)

wherein $Y^1$ and $Y^2$ each independently represent an aryl group which may have at least one substituent, or bond each other to from a saturated ring in which nitrogen and carbon atoms are embedded; and $B^1$ represents a cyclic active methylene structure.

[16] The ultraviolet absorber of [15], wherein, in formula (IV), $B^1$ is one selected from the above-described Active Methylene Group (II).

[17] The ultraviolet absorber of [15] or [16], wherein, in formula (IV), $Y^1$ and $Y^2$ each independently represent an aryl group which may have at least one substituent.

[18] An ultraviolet absorber comprising at least one compound represented by formula (V) or (VII):

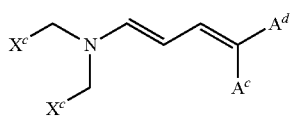
(V)

wherein $X^c$ represents cyano or an alkyl-oxycarbonyl; and $A^c$ and $A^d$ each independently represent an alkyl- or aryl-carbonyl group, alkyl-oxycarbonyl group or cyano, or bond each other to form one selected from the above-described Active Methylene Group (II):

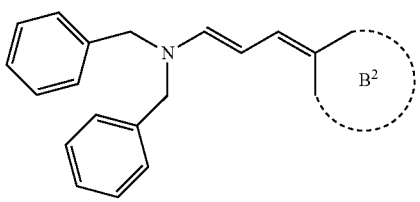

where, in formula, $B^2$ represents one selected from the above-described Active Methylene Group (II).

[19] The ultraviolet absorber of [18], wherein the compound represented by formula (V) is a compound represented by formula (VI):

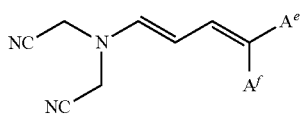

wherein $A^e$ and $A^f$ each independently represent an alkyl- or aryl-carbonyl group, alkyl-oxycarbonyl group, or cyano, or bond each other to form a ring selected from the above-described Active Methylene Group (II).

[20] A merocyanine compound represented by formula (V):

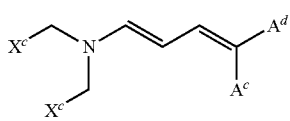

wherein $X^c$ represents cyano or an alkyl-oxycarbonyl; and $A^c$ and $A^d$ each independently represent an alkyl- or aryl-carbonyl group, alkyl-oxycarbonyl group or cyano, or bond each other to form one selected from the above-described Active Methylene Group (II).

[21] A merocyanine compound represented by formula (VI):

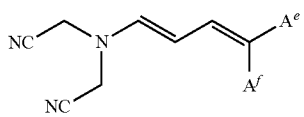

wherein $A^e$ and $A^f$ each independently represent an alkyl- or aryl-carbonyl group, alkyl-oxycarbonyl group, or cyano, or bond each other to form a ring selected from the above-described Active Methylene Group (II).

[22] A merocyanine compound represented by formula (VII):

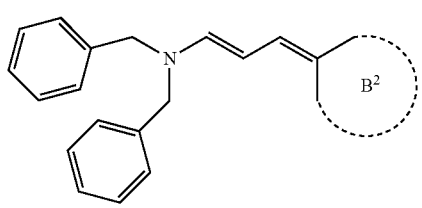

where, in formula, $B^2$ represents one selected from the above-described Active Methylene Group (II).

[23] A process of preparing a merocyanine compound represented by formula (VI), comprising reacting a monohydrochloride represented by formula (VI-a) and/or a dihydrochloride represented by formula (VI-b) and an active methylene compound:

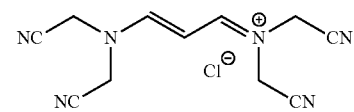

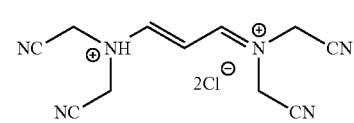

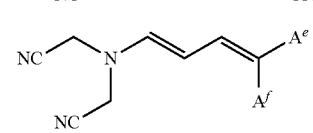

wherein $A^e$ and $A^f$ each independently represent an alkyl- or aryl-carbonyl group, alkyl-oxycarbonyl group, or cyano, or bond each other to form a ring selected from Active Methylene Group (II):

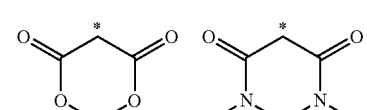

where, in formulas, "*" indicates a portion linking to formula (I); $R^0$ and $R^1$ each independently represent a hydrogen atom or an alkyl or phenyl group which may have at least one substituent, or bond each other to form a ring; and X represents an oxygen or sulfur atom.

According to the invention, it is possible to provide an ultraviolet-absorbable polymer film and a merocyanine-series ultraviolet absorber, having high light-fastness.

And, according to the invention, it is possible also to provide novel merocyanine compounds useful in various usages such as an ultraviolet absorber, and a process for preparing them.

DETAILED DESCRIPTION OF THE INVENTION

The invention is described in detail hereinunder. In this description, the numerical range expressed by the wording "a number to another number" means the range that falls between the former number indicating the lowermost limit of the range and the latter number indicating the uppermost limit thereof.

1. Polymer Film

The invention relates to a polymer film comprising at least one compound represented by formula (I). The compound represented by formula (I) is a merocyanine compound having an ultraviolet absorbing ability. Conventional merocyanine-series ultraviolet absorbers don't have sufficient light-fastness, and they suffer from the problem that their ultraviolet-absorbing abilities decrease over time. The compound represented by formula (I) has higher light-fastness, compared with conventional merocyanine-series ultraviolet absorbers.

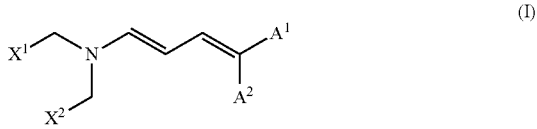

(I)

In formula (I), $A^1$ and $A^2$ each independently represent a group having a Hammett's σp value of 0.2 or more, or bond each other to form a cyclic active methylene structure; and $X^1$ and $X^2$ each independently represent a hydrogen atom, aryl group, hetero-cyclic group, cyano, N-alkyl- or N-aryl-carbamoyl, or alkyl- or aryl-oxycarbonyl, or bond each other to form a saturated ring in which nitrogen and carbon atoms are embedded, and the group and ring may have at least one substituent.

In the formula, $A^1$ and $A^2$ each independently represent a group having a Hammett's σp value of 0.2 or more, or bond each other to form a cyclic active methylene structure. The Hammett's rule is an empirical rule advocated by L. P. Hammett in 1935 so as to quantitatively discuss the effect of substituent on the reaction or equilibrium of benzene derivatives and its propriety is widely admitted at present. The substituent constant determined by the Hammett's rule includes a σp value and a σm value and these values can be found in a large number of general publications and described in detail, for example, in J. A. Dean (compiler), Lange's Handbook of Chemistry, 12th ed., McGraw-Hill (1979), Kagakuno Ryoiki (Chemistry Region), special number, No. 122, pp. 96-103, Nankodo (1979), and Chem. Rev., 1991. No. 91, pp. 165-195. The group having a Hammett's σp value of 0.2 or more means an electron-withdrawing group. The σp value is preferably equal to or more than 0.25, more preferably equal to more than 0.3, or further more preferably equal to or more than 0.35.

Examples of the group having a Hammett's σp value of 0.2 or more include cyano (0.66), a carboxy group (—COOH: 0.45), an alkoxycarbonyl group (—COOMe:0.45), an aryloxycarbonyl (—COOPh:0.44), a carbamoyl (—CONH$_2$: 0.36), an alkyl-carbonyl (—COMe:0.50), an aryl-carbonyl group (—COPh:0.43), an alkyl-sulfonyl group (—SO$_2$Me: 0.72) and an aryl-sulfonyl group (—SO$_2$Ph:0.68). In the description, "Me" means methyl, and "Ph" means phenyl. The numerical values in parenthesis indicate the σp values of typical groups, as extracted from Chem. Rev., 1991, vol. 91, p. 165 to 195. Examples of the group having a Hammett's σp value of 0.2 or more include also a sulfamoyl group, sulfinyl group, and hetero-cyclic group.

Among the examples, an alkyl- or aryl-carbonyl group, alkyl- or aryl-oxycarbonyl group, alkyl- or aryl-sulfonyl group, N-alkyl- or N-aryl-carbamoyl group, or cyano is preferable.

The alkyl in the alkyl-carbonyl, alky-oxycarbonyl, alkyl-sulfonyl or N-alkyl-carbamoyl group may have a linear or branched chain structure. The alkyl is preferably a $C_{1-30}$ alkyl, more preferably $C_{1-20}$ alkyl, or further more preferably $C_{1-15}$ alkyl.

The aryl in the aryl-carbonyl, aryl-oxycarbonyl, aryl-sulfonyl or N-aryl-carbamoyl group may be a single or condensed ring residue. The aryl is preferably phenyl.

If possible, these groups may have at least one substituent. Examples of the substituent include halogen atoms (for example, fluorine, chlorine, bromine and iodine atoms; alkyls (preferably $C_{1-10}$ alkyls, more preferably $C_{1-5}$ alkyls), alkoxys (preferably $C_{1-10}$ alkoxys, more preferably $C_{1-5}$ alkoxys), alkyloxycarbonyls (preferably $C_{2-11}$ alkyloxycarbonyls, more preferably $C_{2-6}$ alkyloxycarbonyls), and alkylcarbonyloxys (preferably $C_{2-11}$ alkylcarbonyloxys, more preferably $C_{2-6}$ alkylcarbonyloxys).

The active methylene structure formed of bonding $A^1$ and $A^2$ is preferably 5- to 7-membered ring (more preferably 5- or 6-membered ring). The term "active methylene structure" means any structures having methylene, —CH$_2$—, sandwiched between two electron-withdrawing groups. Examples of the cyclic active methylene structure include those exemplified below.

(a) a 1,3-dicarbonyl nucleus, such as 1,3-indanedione nucleus, 1,3-cyclohexanedione, 5,5-dimethyl-1,3-cyclohexanedione, 1,3-dioxane-4,6-dione and Meldrum's acid;

(b) a pyrazolinone nucleus, such as 1-phenyl-2-pyrazolin-5-one, 3-methyl-1-phenyl-2-pyrazolin-5-one, and 1-(2-benzothiazoyl)-3-methyl-2-pyrazolin-5-one;

(c) an isoxazolinone nucleus, such as 3-phenyl-2-isoxazolin-5-one, and 3-methyl-2-isoxazolin-5-one;

(d) an oxyindole nucleus, such as 1-alkyl-2,3-dihydro-2-oxyindole, (e) a 2,4,6-triketohexahydropyrimidine nucleus, such as barbituric acid, 2-thiobarbituric acid and a derivative thereof; examples of the derivative include a 1-alkyl form such as 1-methyl and 1-ethyl, a 1,3-dialkyl form such as 1,3-dimethyl, 1,3-diethyl and 1,3-dibutyl, a 1,3-diaryl form such as 1,3-diphenyl, 1,3-di(p-chlorophenyl) and 1,3-di(p-ethoxycarbonylphenyl), a 1-alkyl-1-aryl form such as 1-ethyl-3-phenyl, and a 1,3-diheterocyclic substitution form such as 1,3-di(2-pyridyl);

(f) a 2-thio-2,4-thiazolidinedione nucleus, such as rhodanine and a derivative thereof; examples of the derivative include a 3-alkylrhodanine such as 3-methylrhodanine, 3-ethylrhodanine and 3-allylrhodanine, a 3-arylrhodanine such as 3-phenylrhodanine, and a 3-heterocyclic ring-substituted rhodanine such as 3-(2-pyridyl)rhodanine;

(g) a 2-thio-2,4-oxazolidinedione (2-thio-2,4-(3H,5H)-oxazoledione) nucleus, such as 3-ethyl-2-thio-2,4-oxazolidinedione;

(h) a thianaphthenone nucleus, such as 3(2H)-thianaphthenone-1,1-dioxide;

(i) a 2-thio-2,5-thiazolidinedione nucleus, such as 3-ethyl-2-thio-2,5-thiazolidinedione;

(j) a 2,4-thiazolidinedione nucleus, such as 2,4-thiazolidinedione, 3-ethyl-2,4-thiazolidinedione and 3-phenyl-2,4-thiazolidinedione;

(k) a thiazolin-4-one nucleus, such as 4-thiazolinone and 2-ethyl-4-thiazolinone;

(l) a 4-thiazolidinone nucleus, such as 2-ethylmercapto-5-thiazolin-4-one and 2-alkylphenylamino-5-thiazolin-4-one;

(m) a 2,4-imidazolidinedione (hydantoin) nucleus, such as 2,4-imidazolidinedione and 3-ethyl-2,4-imidazolidinedione;

(n) a 2-thio-2,4-imidazolidinedione (2-thiohydantoin) nucleus, such as 2-thio-2,4-imidazolidinedione and 3-ethyl-2-thio-2,4-imidazolidinedione;

(o) an imidazolin-5-one nucleus, such as 2-propylmercapto-2-imidazolin-5-one;

(p) a 3,5-pyrazolidinedione nucleus, such as 1,2-diphenyl-3,5-pyrazolidinedione and 1,2-dimethyl-3,5-pyrazolidinedione;

(q) a benzothiophen-3-one nucleus, such as benzothiophen-3-one, oxobenzothiophen-3-one and dioxobenzothiophen-3-one; and (r) an indanone nucleus, such as 1-indanone, 3-phenyl-1-indanone, 3-methyl-1-indanone, 3,3-diphenyl-1-indanone and 3,3-dimethyl-1-indanone.

Preferable examples of the cyclic active methylene structure include a 1,3-dicarbonyl nucleus, pyrazolinone nucleus, 2,4,6-triketohexahydropyrimidine nucleus (including thioketone bodies), 2-thio-2,4-thiazolidinedione nucleus, a 2-thio-2,4-oxazolidinedione, 2-thio-2,5-thiazolidinedione nucleus, 2,4-thiazolidinedione nucleus, 2,4-imidazolidinedione nucleus, 2-thio-2,4-imidazolidinedione nucleus, imidazolin-5-one nucleus, 3,5-pyrazolidinedione nucleus, benzothiophen-3-one nucleus, and indanone nucleus; and more preferable examples of the cyclic active methylene structure include a 1,3-dicarbonyl nucleus, 2,4,6-triketohexahydropyrimidine nucleus (including thioketone bodies), and 3,5-pyrazolidinedione nucleus.

Further more preferably, the cyclic active methylene structure is selected from Active Methylene Group (II):

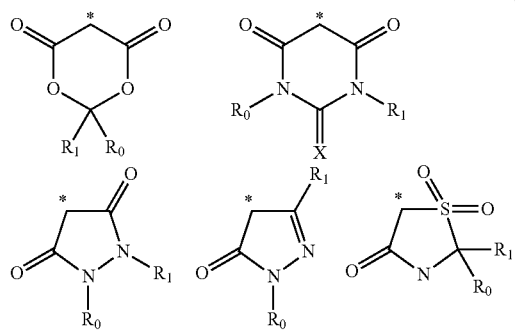

(II)

In formulas, "*" indicates a portion linking to formula (I); $R^0$ and $R^1$ each independently represent a hydrogen atom or an alkyl or phenyl group which may have at least one substituent, or bond each other to form a ring; and X represents an oxygen or sulfur atom.

The alkyl, which may have at least one substituent, represented by $R^0$ or $R^1$ is preferably a $C_{1-10}$ alkyl or more preferably $C_{1-5}$ alkyl such as methyl. The alkyl or phenyl represented by $R^0$ or $R^1$ may have at least one substituent. Examples of the substituent include halogen atoms (for example, fluorine, chlorine, bromine and iodine atoms), alkyloxycarbonyls (preferably $C_{2-11}$ alkyloxycarbonyls, more preferably $C_{2-6}$ alkyloxycarbonyls), and alkoxys (preferably $C_{1-10}$ alkoxys, more preferably $C_{1-5}$ alkoxys).

Among the above-described Active Methylene Group (II), Active Methylene Group (II') shown below

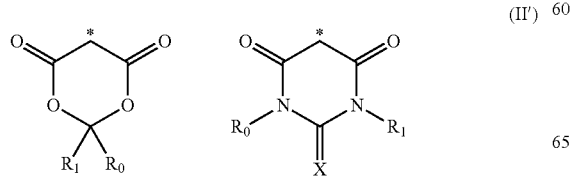

(II')

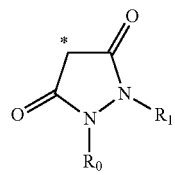

is more preferable; and the following structure

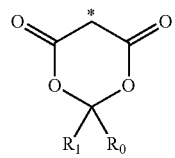

is especially preferable.

In the formulas, $R^0$ and $R^1$ may bond each other to form a ring. Examples of the ring include cyclohexane.

The alkyl or phenyl represented by $R^0$ or $R^1$ or the ring formed by bonding $R^0$ and $R^1$ may have at least one substituent. Examples of the substituent include halogen atoms (for example, fluorine, chlorine, bromine and iodine atoms), alkyloxycarbonyls (preferably $C_{2-11}$ alkyloxycarbonyls, more preferably $C_{2-6}$ alkyloxycarbonyls), and alkoxys (preferably $C_{1-10}$ alkoxys, more preferably $C_{1-5}$ alkoxys).

If $A^1$ or $A^2$ can have at least one substituent, examples of the substituent include residues of merocyanine compounds such as the residue of the compound represented by formula (I). For example, the compound represented by formula (I) may have a structure shown below. In the formula, "$A^{1'}$" represents a divalent group formed by eliminating a hydrogen atom from the group $A^1$.

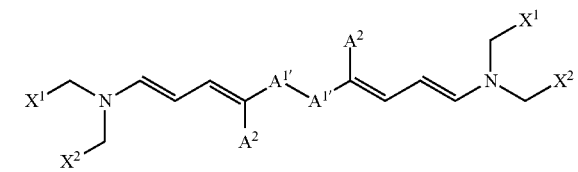

Examples of the group of "-$A^{1'}$-$A^{1'}$-" include the divalent group shown below.
In the formulas, "**" indicates the linking site.

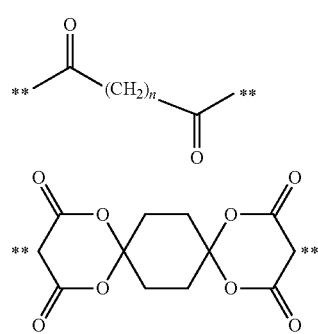

In formula (I), $X^1$ and $X^2$ each independently represent a hydrogen atom, aryl group, hetero-cyclic group, cyano, N-alkyl- or N-aryl-carbamoyl, or alkyl- or aryl-oxycarbonyl, or bond each other to form a saturated ring in which nitrogen and carbon atoms are embedded, and the group and ring may have at least one substituent.

The aryl represented by $X^1$ or $X^2$ may be a single or condensed ring residue. The aryl is preferably phenyl.

The hetero-cyclic group represented by $X^1$ or $X^2$ may be a single or condensed ring residue. The hetero-cyclic group may be aromatic or non-aromatic. At least one hetero atom embedded in the hetero-cyclic group is not limited, and may be a nitrogen, oxygen or sulfur atom. 5- to 7-membered hetero-cyclic group is preferable, and 5- or 6-membered hetero-cyclic group is more preferable.

The alkyl in the N-alkyl-carbamoyl or alkyl-oxycarbonyl group represented by $X^1$ or $X^2$ is preferably a $C_{1-10}$ alkyl, or more preferably $C_{1-5}$ alkyl. Specific examples of the alkyl include methyl, ethyl, propyl and butyl; and ethyl is especially preferable.

The aryl in the N-aryl-carbamoyl or aryl-oxycarbonyl group represented by $X^1$ or $X^2$ may be a single or condensed ring residue. The aryl is preferably phenyl.

The saturated ring formed by bonding $X^1$ and $X^2$ is preferably a 5- to 7-membered ring, or more preferably 5- or 6-membered ring. Examples of the saturated ring include piperidine ring, piperazine ring, pyrrolidine (tetrahydropyrrole) ring; piperidine ring and pyrrolidine ring are preferable; and piperidine ring is more preferable.

The ring formed by bonding $X^1$ and $X^2$ may have at least one substituent. Examples of the substituent include alkyls (preferably $C_{1-10}$ alkyls, more preferably $C_{1-5}$ alkyls), halogen atoms (for example, fluorine, chlorine, bromine and iodine atoms), alkyloxycarbonyls (preferably $C_{2-11}$ alkyloxycarbonyls, more preferably $C_{2-6}$ alkyloxycarbonyls), and alkoxys (preferably $C_{1-10}$ alkoxys, more preferably $C_{1-6}$ alkoxys).

If $X^1$ or $X^2$ can have at least one substituent, examples of the substituent include residues of merocyanine compounds such as the residue of the compound represented by formula (I). For example, the compound represented by formula (I) may have a structure shown below. In the formula, "$X^{1\prime}$" represents a divalent group formed by eliminating a hydrogen atom from the group $X^1$.

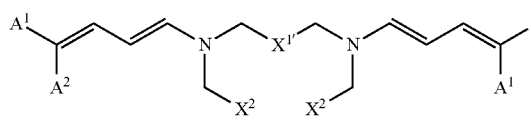

Examples of the $X^{1\prime}$ include phenylene and the groups shown below.

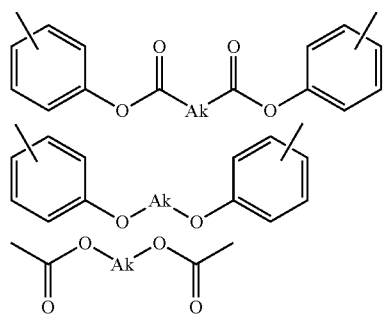

In the formulas, Ak represents a $C_{2-10}$ alkyl or alkyleneoxy.

Preferably, $X^1$ and $X^2$ represent the same group selected from the above-described groups or bond each other to form a ring.

A merocyanine compound such as the compound represented by formula (I) has a donor nucleus (basic nucleus) containing a nitrogen atoms) at the one terminal of the conjugated system, and an acceptor nucleus (acidic nucleus) at the another terminal of the conjugated system. The present inventors conducted various studies, and as a result, they found that the compounds, having any one of those shown below as a donor nucleus, showed improved light-fastness. As shown in JP-A-2009-67973, the previous attempts for improving the light-fastness of the merocyanine compounds have been mainly performed by inserting the partially-conjugated ring. It hasn't been known that the donor nucleus structure of a merocyanine compound influents the light-fastness. The present inventors conducted various studies, and as a result, they found that.

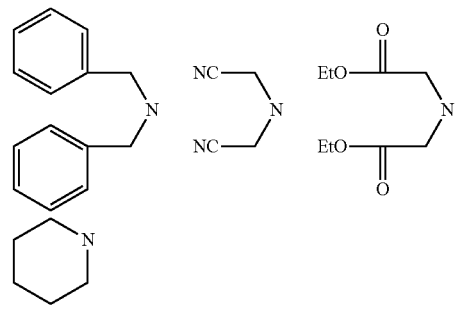

Furthermore, by combining each of the above shown donor nucleuses and the specific acceptor nucleus, the light-fastness can be further improved. Some preferable examples will be described below.

Preferable examples of the compound represented by formula (I) include the compound represented by formula (III).

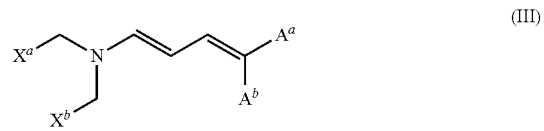

(III)

In formula (III), $X^a$ and $X^b$ each independently represent cyano or an alkyl- or aryl-oxycarbonyl, which may have at least one substituent. Preferable examples of the alky- or aryl-oxycarbonyl group and of its substituent include those exemplified as examples of the alkyl- or aryl-oxycarbonyl represented by $X^1$ or $X^2$ in formula (I) and as examples of its substituent.

In formula (III), $A^a$ and $A^b$ each independently represent a group having a Hammett's σp value of 0.2 or more, or bond each other to form a cyclic active methylene structure. The definition of $A^a$ or $A^b$ is same as that of $A^1$ or $A^2$ in formula (I); and preferable examples thereof are same as those of $A^1$ or $A^2$ in formula (I).

It is preferable that $A^a$ and $A^b$ each independently represent an alkyl- or aryl-carbonyl group, alkyl- or aryl-oxycarbonyl group, alkyl- or aryl-sulfonyl group, N-alkyl- or N-aryl-carbamoyl, or cyano, which may have at least one substituent, or bond each other to form a ring selected from the above-described Active Methylene Group (II).

Definitions and preferable examples of the groups represented by $A^a$ or $A^b$ and of the Active Methylene Group (II) formed by bonding $A^a$ and $A^b$ are same as those described above for $A^1$ and $A^2$ in formula (I).

Preferable examples of the compound represented by formula (I) include the compound represented by formula (IV).

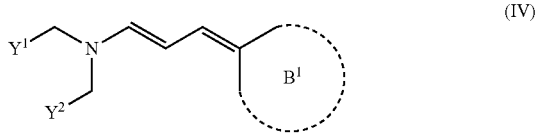

(IV)

In formula (IV), $Y^1$ and $Y^2$ each independently represent an aryl group which may have at least one substituent, or bond each other to from a saturated ring in which nitrogen and carbon atoms are embedded; and $B^1$ represents a cyclic active methylene structure.

Preferable examples of the aryl group represented by $Y^1$ or $Y^2$ and of its substituent are same as those of the aryl group represented by $X^1$ or $X^2$ in formula (I), or that is, phenyl is preferable.

Preferable examples of the saturated ring formed by bonding $Y^1$ and $Y^2$ are same as those of the saturated ring formed by bonding $X^1$ and $X^2$ in formula (I), or, that is, piperidine ring is preferable.

Both of $Y^1$ and $Y^2$ preferably represent an aryl group, and both of $Y^1$ and $Y^2$ more preferably represent phenyl.

The cyclic-active methylene structure represented by $B^1$ is preferably any one of the above-described Active Methylene Group (II).

Preferable examples of the compound represented by formula (I) include the compound represented by formula (V).

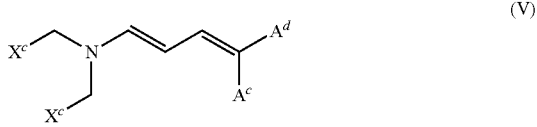

(V)

In formula (V), $X^c$ represents cyano or an alkyl-oxycarbonyl; and $A^c$ and $A^d$ each independently represent an alkyl- or aryl-carbonyl group, alkyl-oxycarbonyl group or cyano, or bond each other to form one selected from the above-described Active Methylene Group (II).

Preferable examples of the alkyl-oxycarbonyl group represented by $X^C$ are same as those of the alkyl-oxycarbonyl group represented by $X^1$ or $X^2$ in formula (I).

Preferable examples of the alkyl- or aryl-carbonyl group, and the alkyl-oxycarbonyl group represented by $A^c$ or $A^d$ are same as those of the alkyl- or aryl-carbonyl group, and the alkyl-oxycarbonyl group represented by $A^1$ or $A^2$ in formula (I).

Preferable examples of the compound represented by formula (I) or (V) include the compound represented by formula (VI).

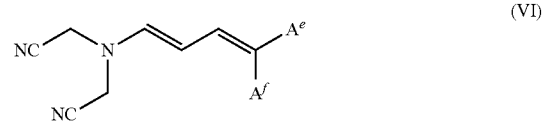

(VI)

In formula (VI), $A^e$ and $A^f$ each independently represent an alkyl- or aryl-carbonyl group, alkyl-oxycarbonyl group, or cyano, or bond each other to form a ring selected from the above-described Active Methylene Group (II).

Preferable examples of the alkyl- or aryl-carbonyl group, and the alkyl-oxycarbonyl group represented by $A^e$ or $A^f$ are same as those of the alkyl- or aryl-carbonyl group, and the alkyl-oxycarbonyl group represented by $A^1$ or $A^2$ in formula (I).

Preferable examples of the compound represented by formula (I) include the compound represented by formula (VII).

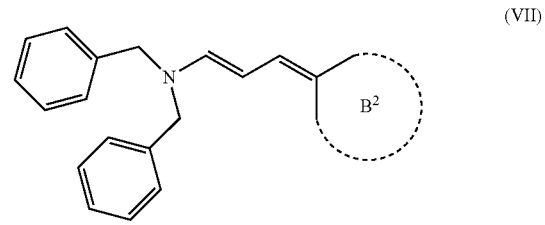

(VII)

In formula, $B^2$ represents one selected from the above-mentioned Active Methylene Group (II).

Examples of the compound represented by formula (I) include, but are not limited, those shown below.

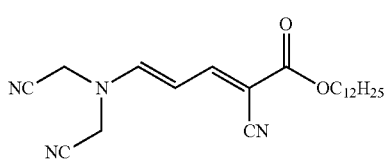

M-1

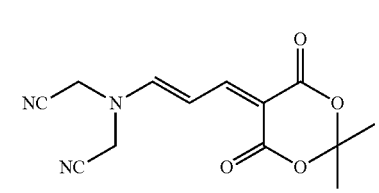

M-2

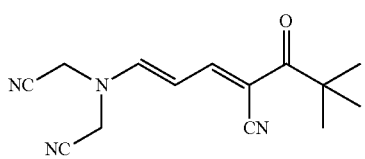

M-3

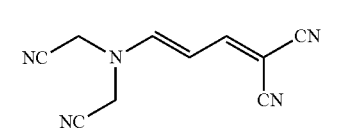

M-4

-continued
M-5
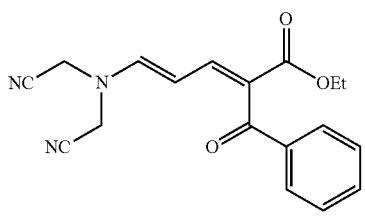
M-6
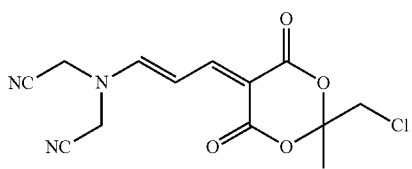
M-7
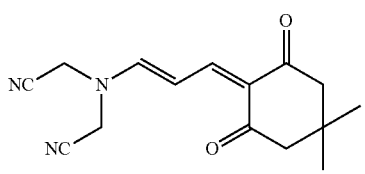
M-8
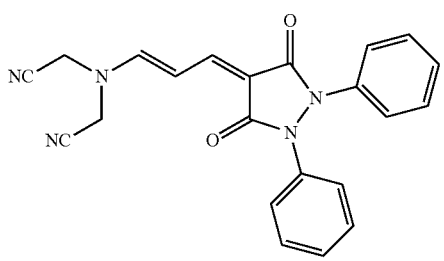
M-9
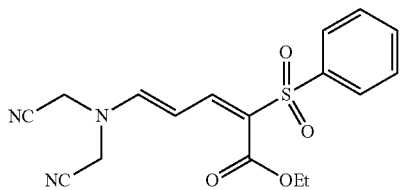
M-10
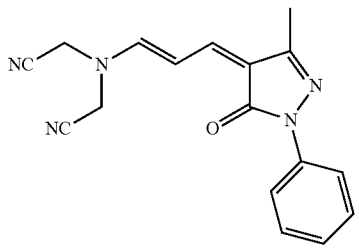
M-11
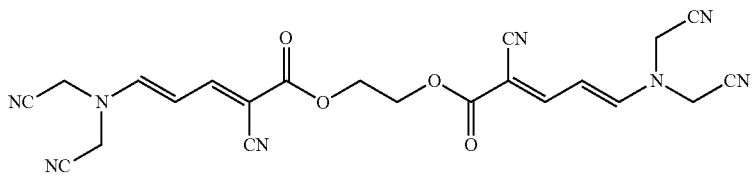
M-12
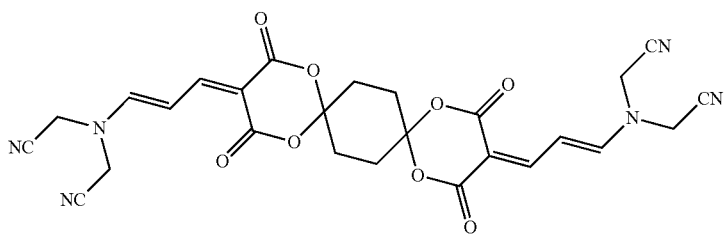
M-13
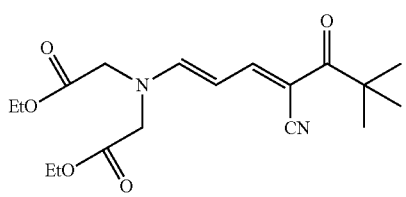
M-14
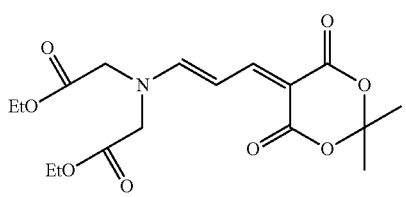
M-15
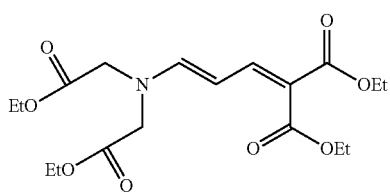
M-16
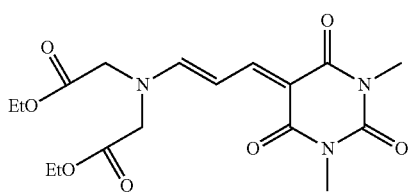

-continued
M17
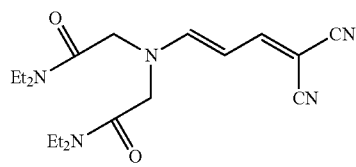
M-18
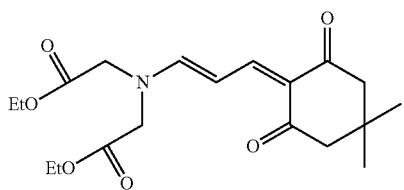
M-19
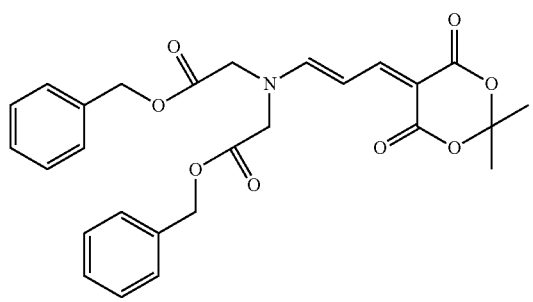
M-20
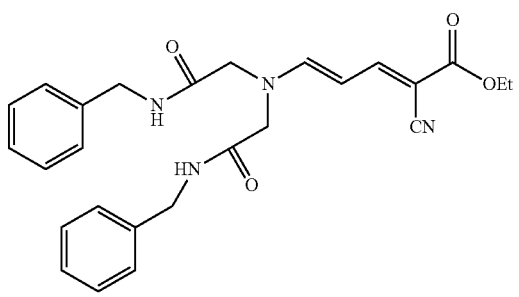
M-21
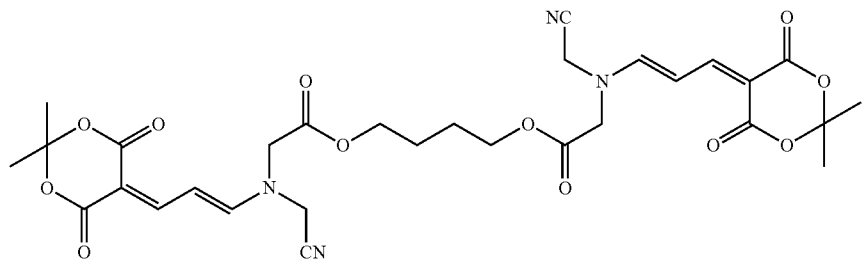
M-22
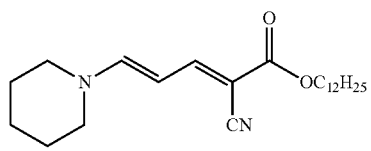
M-23
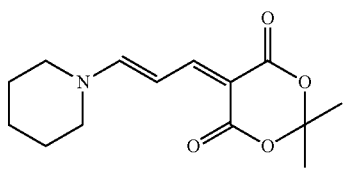
M-24
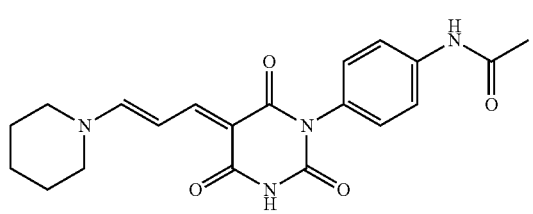
M-25
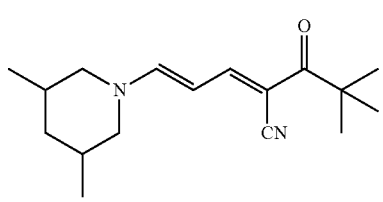
M-27
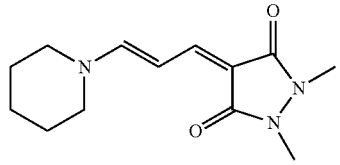
M-28
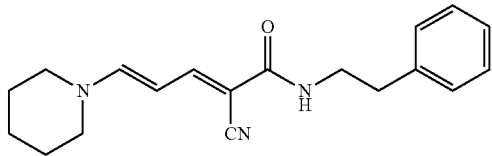
M-29
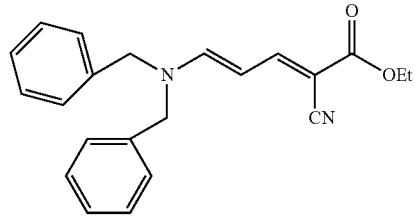
M-30
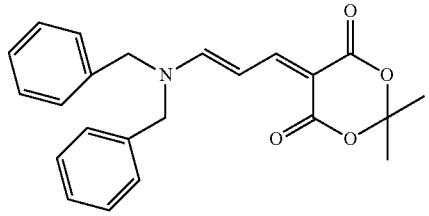

-continued

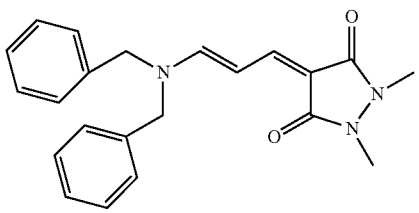
M-31

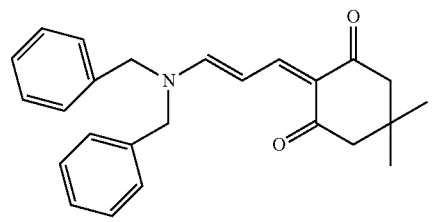
M-32

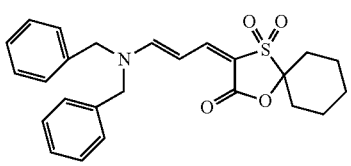
M-34

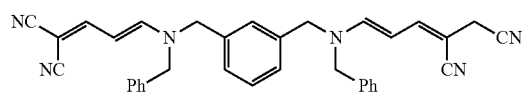
M-35

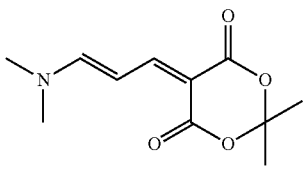
M-36

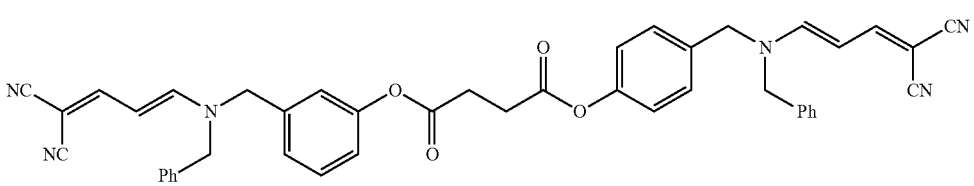
M-37

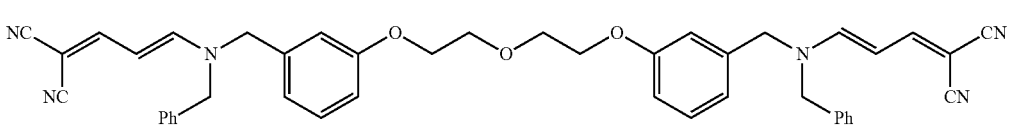
M-38

The compound represented by formula (I) may be prepared according to any method. One example is as follows. N-[3-(phenylamino)-2-propenylidene]aniline monohydrochloride is prepared as a starting material, reacted with an active methylene compound to insert the acceptor nucleus, and then reacted with an amine agent to insert the donor nucleus. In this way, the compound of formula (I) can be prepared. The method using a streptocyanine compound as a starting material is also known, as described in Japanese Patent No. 3973941.

However, the present inventors conducted various studies, and as a result, they found that the compound represented by formula (VI) was not obtainable according to the above-described known methods. Even if using an acetate salt of a streptocyanine compound, disclosed in JP-A-2003-95322, as a starting material, the compound of formula (IV) was not obtainable. The present inventors further conducted various studies, and as a result they found that, by reacting a mono-hydrochloride represented by formula (VI-a) and/or a dihydrochloride represented by formula (VI-b) and an active methylene compound, the compound of formula (IV) was obtainable stably with a good yield.

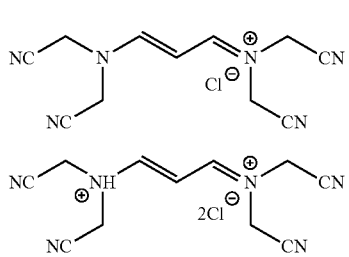

(VI-a)

(VI-b)

The monohydrochloride represented by formula (VI-a) and the dihydrochloride represented by formula (VI-b) may be prepared as follows. Iminoacetonitrile and concentrated hydrochloric acid are mixed in a solvent such as methanol, and are stirred under heat (for example, at 40-60 degrees Celsius), if necessary; and, by adding dropwise 1,1,3,3-tetramethoxypropane thereto, the reaction is carried out to give the monohydrochloride and the dihydrochloride. The reaction is preferably carried out according to heating-reflux. By adjusting the reaction condition, either of monohydrochloride represented by formula (VI-a) or the dihydrochloride represented by formula (VI-b) may be prepared preferentially. According to the process of the present invention, using the monohydrochloride represented by formula (VI-a) is preferable. Of course, the reactant containing the dihydrochloride represented by formula (VI-b) may be used.

Next, a monohydrochloride represented by formula (VI-a) and/or a dihydrochloride represented by formula (VI-b), an active methylene compound, and a base are reacted to insert an acceptor nucleus. The reaction solvent is preferably selected from alcohols such as methanol, ethanol and 2-propanol. The reaction is preferably carried out at a temperature of from 60 to 90 degrees Celsius for about 1-2 hours. The active methylene compound to be reacted may be selected depending on the target acceptor-nucleus structure. For example, the compound selected from the above-described Active Methylene Group (II) may be used as a reactive reagent.

The polymer film of the invention may contain the compound represented by the formula (I) in an amount so that the compound brings about the ultraviolet-absorption ability sufficiently. Generally, an amount of the compound is preferably from 0.05 to 10% by mass, or more preferably from 0.1 to 5% by mass, with respect to the total mass of the materials contained in the polymer film The major ingredient of the polymer film is not limited. Any materials may be used so far as they are processable into a film form. The major ingredient may be selected from any polymers depending on the usage. Examples of the polymer which can be used in the invention include cellulose series polymers such as cellulose triacetate; polycarbonate series polymers; polyester series polymers such as polyethylene terephthalate and polyethylene naphthalate; acryl series polymer such as polymethylmethacrylate; and styrene series polymers such as polystyrene and acrylonitrile-styrene copolymer (AS polymer). Examples of the polymer which can be used in the invention include also polyolefins such as polyethylene and polypropylene; polyolefin series polymer such as ethylene-propylene copolymer; vinyl chloride series polymers; amide series polymers such as nylon and aromatic polyamide; imide series polymers, sulfone series polymers; polyethersulfone series polymers; polyether ether ketone series polymers; polyphenylene sulfide series polymers; vinylidene chloride series polymers; vinyl alcohol series polymers; vinyl butyral series polymers; allirate series polymers; polyoxymethylene series polymers; epoxy series polymers; and any mixed polymers thereof.

The method for preparing the polymer film of the invention is not limited. And any known methods such as a solution film-forming method and a melt film-forming method may be used.

The polymer film of the invention may contain other ultraviolet absorber(s) along with the compound represented by formula (I). The polymer film of the invention may contain other additive(s) such as a plasticizer, anti-degradation agent (for example, antioxidant, peroxide decomposer, radical-inhibitor, metal deactivator, oxygen-trapping agent, or amine), and organic and/or inorganic fine particles.

The compound represented by formula (I) has no absorption in the visible light region, and it is possible to prepare the polymer film of the invention as a transparent polymer film by selecting the polymer to be used along with the compound. The polymer film has an ultraviolet absorbing ability by containing the compound of formula (I), and is useful in various usages such as protective films for various members, anti-insect films, films for solar cell modules and films for architectural materials.

2. Retardation Plates

The present invention relates also to the retardation plate (retardation film) comprising a polymer of the invention and an optically anisotropic layer of a cured liquid crystal composition. The retardation plate may have two or more optically anisotropic layers of a cured liquid crystal composition. The retardation plate is useful for optical compensation of liquid crystal display devices employing any mode such as a TN mode. One example of the optically anisotropic layer is an optically anisotropic layer formed of a liquid crystal composition cured in a hybrid alignment state. Preferable example is an optically anisotropic layer formed of a liquid crystal composition containing a discotic liquid crystal compound cured in a hybrid alignment state.

The liquid crystal composition to be used for preparing the optically anisotropic layer is preferably a composition capable of forming a nematic or smectic phase. Generally, liquid crystal compounds are classified into rod-like liquid crystal and discotic liquid crystal depending on the molecular shape, and according to the invention, liquid crystal compounds having any shape may be used.

The optically anisotropic layer may be prepared as follows. A composition, containing at least one liquid crystal compound, is applied to a surface of a polymer film or an alignment layer formed thereon, is aligned in a desired alignment state, and is cured by polymerization to fix the alignment state. The optically anisotropic layer is preferably formed by curing the hybrid alignment state of liquid crystal molecules (including discotic and rod-like liquid crystal molecules). The term "hybrid alignment" means the alignment in which directors of liquid crystal molecules vary along the thickness direction. Rod-like liquid crystal molecules have a director along their long axes, and discotic liquid crystal molecules have a director along the normal directions of their discotic planes.

For aligning liquid crystal molecules in a desired alignment state, and for improving the coating- or curing-ability of the composition, at least one additive may be added to the composition. The composition is preferably curable, and is more preferably curable by polymerization or cross-linking. Accordingly, the composition may contain a polymerization initiator, polymerizable monomer, cross-linking agent or the like.

The composition may be prepared as a coating liquid, be applied to a surface of an alignment layer formed on the polymer film to be used as a support, be dried to remove the solvent, be aligned in a desired alignment state, and then cured by polymerization to form an optically anisotropic layer. Examples of the alignment layer which can be used in the invention include polyvinyl alcohol layers and polyimide layers.

Next, the polymerization may be carried out by irradiation with ultraviolet light or the like to fix the alignment state. In this way, the optically anisotropic layer is formed. Ultraviolet light is preferably used in irradiation for the polymerization.

The thickness of the optically anisotropic layer is not limited, generally is preferably from about 0.1 to about 10 micro meters, or more preferably from about 0.5 to about 5 micro meters.

3. Ultraviolet Absorber

The present invention also relates to an ultraviolet absorber comprising (preferably consisting essentially of) at least one compound represented by formula (III) or (IV). Preferable examples of the ultraviolet absorber are same as those described above. One examples of the ultraviolet absorber is an ultraviolet absorber comprising (preferably consisting essentially of) at least one compound represented by any one of formulas (V)-(VII).

The ultraviolet absorber of the invention exhibits not only a good ultraviolet absorbing ability but also higher light-fastness compared with the conventional merocyanine-series ultraviolet absorbers. Namely, the ultraviolet absorber of the invention exhibits smaller decrease in the ultraviolet absorbing ability by irradiation with light compared with the conventional merocyanine-series ultraviolet absorbers.

The ultraviolet absorber of the invention is useful as an ultraviolet absorber for polymer films. The ultraviolet absorber of the invention is useful also as an ultraviolet absorber for liquids, powders and solids to be used in various usages such as glass plates, glass containers, plastic substrates, plastic containers, fibers, papers, inks, paints and architectural materials. The ultraviolet absorber of the invention may be used by mixing any matrix formed of any material and having any shape. The ultraviolet absorber of the invention may be dispersed or dissolved in the matrix, or adsorbed chemically or physically on the matrix.

4. Merocyanine Compounds

The present invention relates also to the compounds represented by formulas (V)-(VII). The merocyanine compounds of the invention are useful as an ultraviolet absorber. The merocyanine compounds of the invention are useful as an optically anisotropic material.

EXAMPLES

Paragraphs below will further specifically describe features of the present invention, referring to Examples and Comparative Examples. Any materials, amount of use, ratio, details of processing, procedures of processing and so forth shown in Examples may appropriately be modified without departing from the spirit of the present invention. Therefore, it is to be understood that the scope of the present invention should not be interpreted in a limited manner based on the specific examples shown below.

In the following description, "Ac" and "Ph" means acetyl and phenyl respectively.

1. Examples of Preparing Compounds of Formula (I)

(1) Synthesis of Exemplified Compound M-30

Compounds of formula (I) were prepared according to any one of Synthetic Routes A-D. Some examples are shown below.

(1) Example of Preparing Compound M-30

Route A

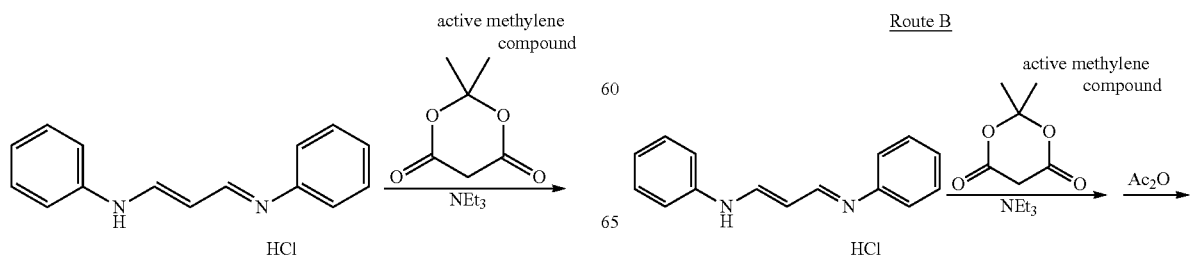

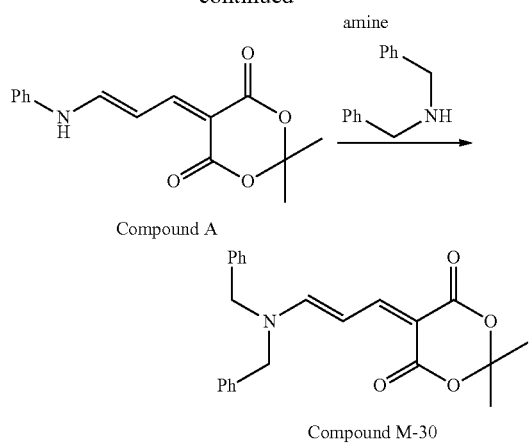

Compound A

Compound M-30

(Synthesis of Compound A)

In methanol (75 mL), N-[3-(phenylamino)-2-propenylidene]aniline monohydrochloride (26 g) and Meldrum's Acid (16 g) were mixed and stirred at a room temperature, and, after being added dropwise with triethylamine (16 mL), heated to reflux for an hour. The reaction liquid was cooled to a room temperature, and then 12 g of Compound A was obtained (the yield 44%) by filtration of the crystals. The determination of the synthesized compound was performed by $^1$H-NMR.

$^1$H-NMR (400 MHz, CDCl$_3$): δ1.75 (s, 6H), δ7.2 (m, 1H), δ7.35 (d, 2H), δ7.4 (m, 2H), δ7.7 (t, 1H), δ8.0 (t, 1H), δ8.2 (d, 1H), δ10.8 (bd, 1H).

(Synthesis of Exemplified Compound M-30)

In ethanol (50 mL), Compound A (12 g) and dibenzylamine (22 mL) were heated to reflux for three hours; and then the solvent was evaporated by using a rotary evaporator. By adding with 100 Ml of a mixed solvent of methanol/water (5/1), the reaction mixture was crystallized again from the mixed solvent.

In this way, 13 g of Compound M-30 (the yield 73%) was obtained. The determination of the synthesized compound was performed by $^1$H-NMR.

$^1$H-NMR (400 MHz, CDCl$_3$): δ1.7 (s, 6H), δ4.48 (s, 2H), δ4.55 (s, 2H), δ7.15 (m, 2H), δ7.2-7.3 (m, 1H+2H), δ7.35-7.45 (m, 6H), δ7.52 (d, 1H), δ8.05 (d, 1H).

(2) Synthesis of Exemplified Compound M-14

Route B

-continued

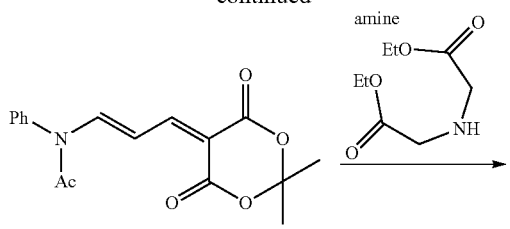

Compound B

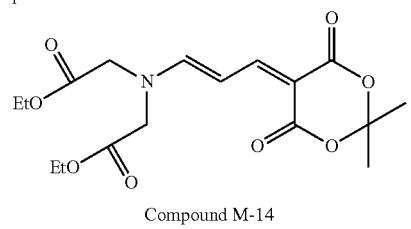

Compound M-14

(Synthesis of Compound B)

In pyridine (10 mL), Compound A (8.2 g) was stirred at a room temperature, and, after being added dropwise with anhydrous acetic acid (3.8 mL), was stirred at 90 degrees Celsius for an hour. The reaction liquid was added with 100 mL of a mixed solvent of methanol/water (1/1) while being cooled by using a bath containing iced water, and then 8.5 g of Compound B was obtained (the yield 90%) by filtration of the crystals. The determination of the synthesized compound was performed by $^1$H-NMR.

$^1$H-NMR (400 MHz, CDCl$_3$): δ1.65 (s, 6H), δ2.02 (s, 3H) δ6.6 (t, 1H), δ7.22 (m, 2H), δ7.5-7.6 (m, 3H), δ8.15 (d, 1H), δ8.5 (d, 1H).

(Synthesis of Exemplified Compound M-14)

In ethanol (10 mL), Compound B (2.0 g) and iminodiacetic acid diethyl ester 2.2 mL) were heated to reflux for three hours, and then the solvent was evaporated by using a rotary evaporator. The product was subjected to a silica-gel column chromatography treatment, and 0.8 g of Compound M-14 (the yield 34%) was obtained. The determination of the synthesized compound was performed by $^1$H-NMR.

$^1$H-NMR (400 MHz, CDCl$_3$): δ1.32 (t, 6H), δ1.7 (s, 6H), δ4.0 (s, 2H), δ4.22 (s, 2H), δ64.25 (q, 4H), δ6.9 (t, 1H), δ7.25 (d, 1H), δ8.0 (d, 1H).

(3) Synthesis of Exemplified Compound M-22

Route C

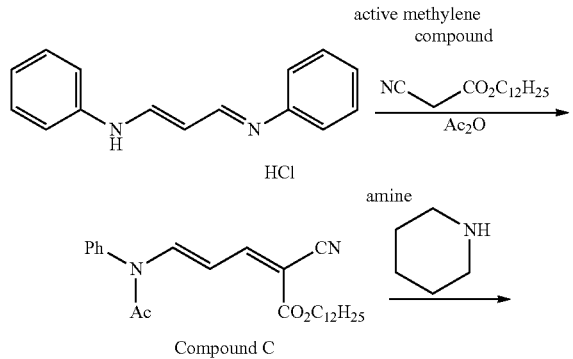

Compound C

-continued

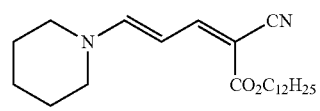

Compound M-22

(Synthesis of Compound C)

N-[3-(phenylamino)-2-propenylidene]aniline monohydrochloride (7.7 g) and cyanoacetic acid n-dodecyl (7.6 g) were added to anhydrous acetic acid (15 mL), and were stirred at 110 degrees Celsius for an hour. The reaction liquid was cooled to a room temperature, and was added dropwise to iced water. The precipitated crystals were filtered out, and then were crystallized again from added methanol. In this way, 6.7 g of Compound C was obtained (the yield 53%). The determination of the synthesized compound was performed by $^1$H-NMR.

$^1$H-NMR (400 MHz, CDCl$_3$): δ0.9 (t, 3H), δ1.25-1.4 (m, 18H), δ1.65-1.75 (m, 2H), δ2.0 (s, 3H), δ4.2 (t, 2H), δ5.5 (t, 1H), δ7.2 (d, 2H), δ7.55-7.6 (m, 3H), δ7.9 (d, 1H), δ8.35 (d, 1H).

(Synthesis of Exemplified Compound M-22)

In ethanol (10 mL), Compound C (1.8 g) and piperidine Dibenzylamine (1.3 mL) were heated to reflux for three hours. The reaction liquid was cooled to a room temperature, and, after being added with water (10 mL), the precipitated crystals were filtered out, and were crystallized again from a mixed solvent of methanol/water (1/1). In this way, 12 g of Compound M-22 was obtained (the yield 82%). The determination of the synthesized compound was performed by $^1$H-NMR.

$^1$H-NMR (400 MHz, CDCl$_3$): δ0.9 (t, 3H), δ1.2-1.4 (m, 18H), δ1.6-1.75 (m, 8H), δ3.4 (m, 4H), δ4.15 (t, 2H), δ5.65 (t, 1H), δ7.0 (d, 1H), δ7.8 (d, 1H).

(4) Synthesis of Exemplified Compound M-2

Route D

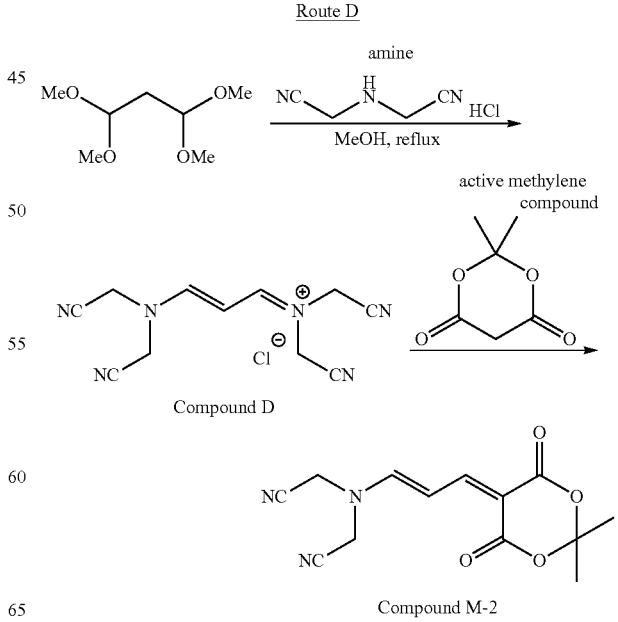

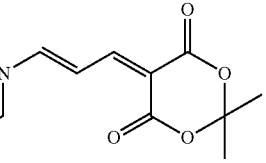

Compound M-2

(Synthesis of Compound D)

In methanol (80 mL), iminodiacetonitrile (20 g) and concentrated hydrochloric acid (10 mL) were stirred, and were added dropwise with 1,1,3,3-tetramethoxy propane (17.4 mL) for 20 minutes. The reaction liquid was heated to reflux for 30 minutes, was cooled to a room temperature, and then the precipitated crystals were filtered out. In this way, 26 g of Compound D was obtained (the yield 91%). The determination of the synthesized compound was performed by $^1$H-NMR.

$^1$H-NMR (400 MHz, DMSO-d6): δ3.75 (s, 4H), δ4.65 (s, 4H), 5.4-5.45 (m, 1H), δ7.52 (d, 1H), δ9.15 (d, 1H).

It is to be noted that, according to the above-described reaction condition for synthesizing Compound D, Compound E, dihydrochloride adduct, may also be obtained along with Compound D.

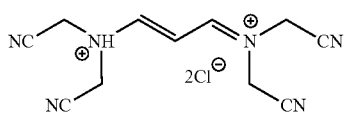

Compound E

In place of Compound D, Compound E may be used for the following process for synthesizing Compound M-2. $^1$H-NMR data of Compound E are shown below.

$^1$H-NMR (400 MHz, DMSO-d6): δ5.1 (s, 8H), δ6.4 (t, 1H), δ8.35 (d, 2H).

(Synthesis of Exemplified Compound M-2)

Compound D (2.4 g) and Meldrum's Acid (1.3 g) were added to methanol (20 mL), and, after being added dropwise with triethylamine (1.7 mL) under stirring, were heated to reflux for 30 minutes. The reaction liquid was cooled to a room temperature, and 1.9 g of Compound M-2 (the yield 76%) was obtained by filtration of the precipitated crystals. The determination of the synthesized compound was performed by $^1$H-NMR.

$^1$H-NMR (400 MHz, DMSO-d6): δ1.64 (s, 6H), δ4.8 (s, 4H), δ7.85 (t, 1H), δ8.0 (d, 1H+1H).

(5) Examples of Preparing other Compounds of Formula (I)

The following exemplified compounds were prepared according to any one of Routes A-D. Regarding each of the synthesized compounds, the synthetic route used for synthesizing each compound and $^1$H-NMR data of each compound are shown below.

Exemplified Compound M-1: Route D; $^1$H-NMR (400 MHz, CDCl$_3$): δ0.9 (t, 3H), δ1.2-1.4 (m, 18H), δ1.65-1.75 (m, 2H), δ4.2 (t, 2H), δ4.25 (s, 4H), δ5.85 (t, 1H), δ6.9 (d, 1H), δ7.8 (d, 1H).

Exemplified Compound M-6: Route D; $^1$H-NMR (400 MHz, DMSO-d6): δ1.7 (s, 3H), δ4.0 (s, 2H), δ4.8 (s, 4H), δ6.85 (t, 1H), δ8.0 (dd, 1H+1H).

Exemplified Compound M-11: Route D; $^1$H-NMR (400 MHz, CDCl$_3$): δ4.25 (s, 4H), δ4.3 (s, 8H), δ5.85 (t, 2H), δ6.9 (d, 2H), δ7.8 (d, 2H).

Exemplified Compound M-12: Route D; The product had poor solubility and therefore, the spectra data were not obtainable.

Exemplified Compound M-23: Route A; $^1$H-NMR (400 MHz, CDCl$_3$): δ1.7 (s, 6H), δ1.7-1.8 (m, 6H), δ3.5 (m, 2H), δ3.6 (m, 2H), δ7.0 (t, 1H), δ7.25 (d, 1H), δ7.95 (d, 1H).

Exemplified Compound M-27: Route C; $^1$H-NMR (400 MHz, CDCl$_3$): δ1.65-1.8 (m, 6H), δ3.15 (s, 6H), δ3.45-3.55 (m, 4H), δ6.9 (t, 1H), δ7.12 (d, 1H), δ7.47 (d, 1H).

Exemplified Compound M-28: Route C; $^1$H-NMR (400 MHz, CDCl$_3$): δ1.6-1.75 (m, 6H), δ2.85 (q, 2H), δ3.3-3.45 (m, 4H), δ3.6 (q, 2H), δ5.6 (t, 1H), δ5.9 (bd, 1H), δ6.95 (d, 1H), δ7.2-7.4 (m, 5H), δ7.85 (d, 1H).

Exemplified Compound M-23: Route C; $^1$H-NMR (400 MHz, CDCl$_3$): δ3.15 (ss, 3H+3H), δ4.5 (s, 2H), δ4.5 (s, 2H), δ7.1 (t, 1H), δ7.15-7.25 (m, 4H), δ7.3-7.45 (m, 5H), 7.55 (d, 1H).

Exemplified Compound M-34: Route A; $^1$H-NMR (400 MHz, CDCl$_3$): δ1.5-1.85 (m, 8H), δ1.9-2.0 (m, 1H), δ2.15-2.25 (m, 1H), δ4.5 (s, 2H), δ4.45 (s, 2H), δ7.05 (t, 1H), δ7.25-7.35 (m, 4H), δ7.3-7.5 (m, 1H+6H), δ7.6 (d, 1H).

Exemplified Compound M-35: Route C; $^1$H-NMR (400 MHz, CDCl$_3$): δ4.4-4.5 (m, 8H), δ5.7-5.95 (m, 4H), δ6.9-7.0 (m, 2H), δ7.1-7.55 (m, 14H).

Exemplified Compound M-36: Route A; $^1$H-NMR (400 MHz, CDCl$_3$): δ1.7 (s, 6H), δ3.15 (s, 3H), δ3.3 (s, 3H), δ6.9 (t, 1H), δ7.3 (d, 1H), δ7.95 (d, 1H).

2. Preparation of Polymer Films and Evaluation Regarding Light-Fastness Thereof

Cellulose acylate films containing each of the merocyanine compounds shown in Table 1 were prepared. More specifically, each of the films was prepared as follows.

At first, Solution A having the following formulation was prepared.

| Formulation of Solution A | |
|---|---|
| Cellulose acetate having the averaged degree of substitution of 2.94 | 100.0 parts by mass |
| Methylene chloride (First Solvent) | 475.9 parts by mass |
| Methanol (Second Solvent) | 113.0 parts by mass |
| Butanol (Third Solvent) | 5.9 parts by mass |
| Ultraviolet absorber (shown in Table 1) | 0.1 parts by mass |
| Citrate ester | 0.01 parts by mass |

Each of cellulose acylate films was prepared according to a solution casting method using each of the prepared solutions. All of the obtained films were transparent.

Absorption spectra of each of the obtained films were measured, and λmax and the half bandwidth were calculated. In the description, "λmax" means a wavelength of an absorption peak within the range from 300 nm to 450 nm; and "half bandwidth" means a value indicating precipitousness of the absorption peak, defined as the following formula:

λ½−λmax

In the formula, "λ½" means a wavelength at which the absorbance is half of the absorbance at λmax provided that the relation of "λ½>λmax" is satisfied. The smaller half bandwidth means more precipitous absorption peak, and more reduced coloration.

Each of the obtained films was irradiated with light having an irradiation amount of 150 W/m$^2$ for 200 hours by "Super Xenon Weather Meter SX75" (manufactured by Suga Test Instruments Co., Ltd.); and the variation in absorbance (Abs) before and after the irradiation test was evaluated. In the irradiation test, an optical film, described in JP-A-2008-116788, [0080]-[0082], was disposed between each of the films and "Super Xenon Weather Meter SX75". On the basis of the obtained absorbance values, the light-resistance ratio (residual ratio) (%) after the irradiation test was calculated according to the following formula, and was shown in Table 1.

{(Absorbance after the irradiation test)/(Absorbance before the irradiation test)}×100

In the formula, "Absorbance" is the value at the wavelength of absorption peak of each of exemplified compounds.

TABLE 1

| | λmax (nm) | Light-resistance Ratio of Absorbance at λmax | Half Bandwidth (nm) | Note |
|---|---|---|---|---|
| M-1 | 349 | 99% | 12 | Formula (VI) |
| M-2 | 376 | 95% | 9 | Formula (VI) |
| M-11 | 347 | 97% | 15 | Formula (VI) |
| M-14 | 387 | 96% | 12 | Formula (V) |
| M-22 | 381 | 63% | 14 | Formula (I) |
| M-23 | 390 | 87% | 12 | Formula (IV) |
| M-24 | 405 | 72% | 12 | Formula (IV) |
| M-27 | 402 | 77% | 12 | Formula (IV) |
| M-30 | 393 | 96% | 12 | Formula (VII) |
| M-31 | 404 | 88% | 13 | Formula (VII) |
| M-35 | 376 | 96% | 19 | Formula (I) |
| Z-1 | 369 | 55% | 15 | — |
| Z-2 | 390 | 9% | 11 | — |
| Z-3 | 352 | 99% | 28 | — |

Comparative Compound Z-1

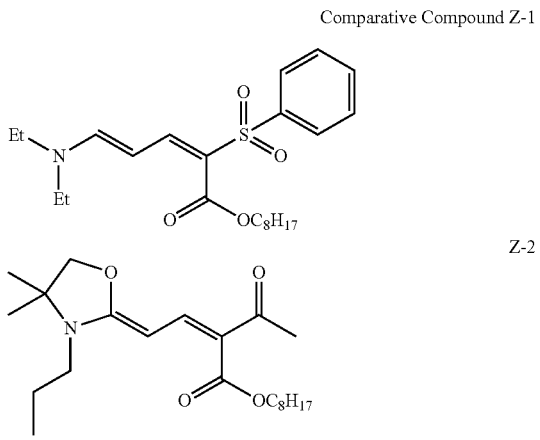

Comparative Compound Z-3

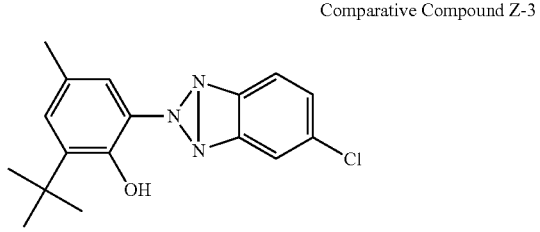 [SMILES: Cc1cc(-n2n3c4ccc(Cl)cc4n23)c(O)c(C(C)(C)C)c1]

(These compounds were prepared according to the above-described Synthetic Route C or the method described in JP-A-2009-67973.)

(Comparative Compound Z-3 is commercially-available as "Tinuvin 329" (Product name; manufactured by Ciba-Japan)

As shown in the above table, it is understandable that the films containing the compound represented by Formula (I) of the invention showed a remarkably higher heat-resistance ratio and were excellent in light-fastness, compared with the films containing the known merocyanine-series ultraviolet absorber.

As shown in the above table, it is understandable that the films containing the compound represented by Formula (I) of the invention had a narrower half bandwidth and a precipitous absorption peak, and were excellent in reduced coloration, compared with the films containing the known benzotriazole-series ultraviolet absorber.

On each of the obtained films of the examples, an optically anisotropic layer was formed by fixing the hybrid alignment of a discotic liquid crystal composition. The prepared laminations were used as an optical compensation film of a TN-mode liquid crystal display device respectively, and it was found that they were appropriate for this usage.

What is claimed is:

1. A polymer film comprising at least one compound represented by formula (I):

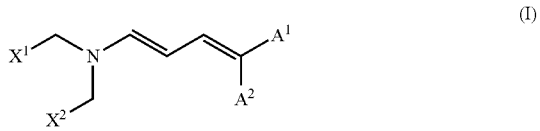

wherein $A^1$ and $A^2$ each independently represent a group having a Hammett's σp value of 0.2 or more, or bond each other to form a cyclic active methylene structure; and $X^1$ and $X^2$ each independently represent a hydrogen atom, aryl group, hetero-cyclic group, cyano, N-alkyl- or N-aryl-carbamoyl, or alkyl- or aryl-oxycarbonyl, or bond each other to form a saturated ring in which nitrogen and carbon atoms are embedded, and the group and ring may have at least one substituent, provided that:

when both of $X^1$ and $X^2$ are cyano, then $A^1$ and $A^2$ each represents cyano, and when both of $X^1$ and $X^2$ are not cyano, then $A^1$ and $A^2$ are bonded to each other to form a ring selected from the following structures, wherein "*" indicates a portion linking to formula (I), and $R_0$ and $R_1$ each independently represents a hydrogen atom or an alkyl or phenyl group which may have at least one substituent, or bond to each other to form a ring:

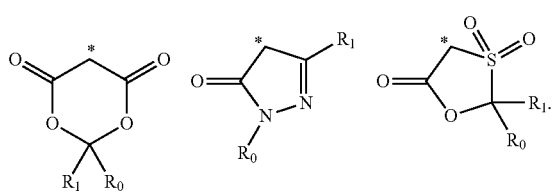

2. A polymer film comprising at least one compound represented by formula (I):

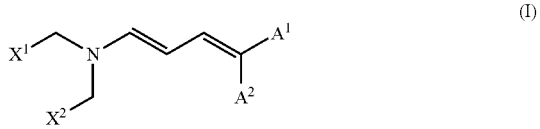

wherein $A^1$ and $A^2$ each independently represent a group having a Hammett's σp value of 0.2 or more, or bond each other to form a cyclic active methylene structure; and $X^1$ and $X^2$ each independently represents an aryl group, alkyl- or aryl-oxycarbonyl or cyano, or bond to each other to form a saturated ring in which nitrogen and carbon atoms are embedded, and the group and ring may have at least one substituent, provided that:

when both of $X^1$ and $X^2$ are cyano, then $A^1$ and $A^2$ each independently represents an alkyl- or aryl-carbonyl group, an alkyl-oxycarbonyl group, or cyano, or bond to each other to form a ring selected from the following Active Methylene Group (II):

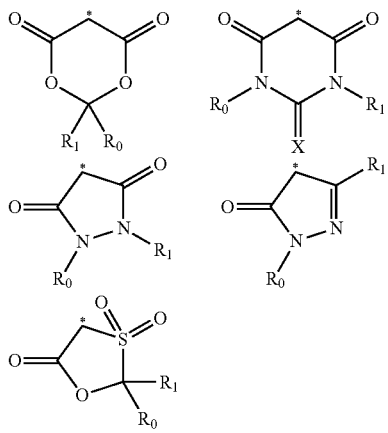
(II)

where, in formulas, "*" indicates a portion linking to formula (I); $R_0$ and $R_1$ each independently represents a hydrogen atom or an alkyl or phenyl group which may have at least one substituent, or bond to each other to form a ring; and X represents an oxygen or sulfur atom, and when both of $X^1$ and $X^2$ are not cyano, then $A^1$ and $A^2$ are bonded to each other to form a ring selected from the following structures, wherein "*", $R_0$ and $R_1$ have the same meanings as above:

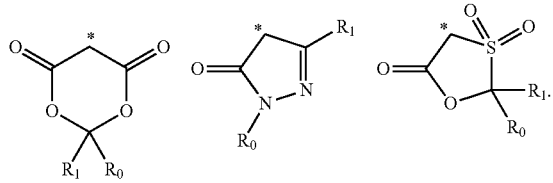

3. A polymer film comprising at least one compound represented by formula (III):

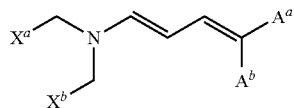
(III)

wherein $X^a$ and $X^b$ each independently represents cyano or an alkyl- or aryl-oxycarbonyl, which may have at least one substituent; and $A^a$ and $A^b$ each independently represents a group having a Hammett's σp value of 0.2 or more, or bond to each other to form a cyclic active methylene structure, provided that:

when both of $X^a$ and $X^b$ are cyano, then $A^a$ and $A^b$ each independently represents an alkyl- or aryl-carbonyl group, an alkyl-oxycarbonyl group, or cyano, or bond to each other to form a ring selected from the following Active Methylene Group (II):

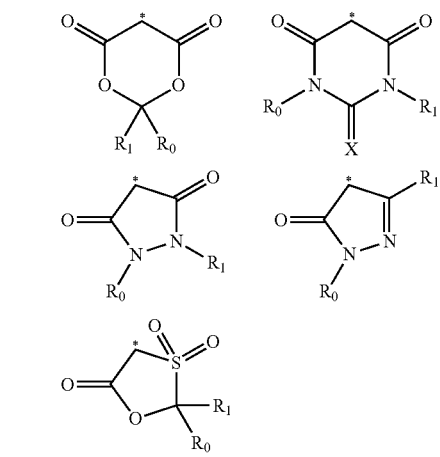
(II)

where, in formulas, "*" indicates a portion linking to formula (III); $R_0$ and $R_1$ each independently represents a hydrogen atom or an alkyl or phenyl group which may have at least one substituent, or bond to each other to form a ring; and X represents an oxygen or sulfur atom, and when both of $X^a$ and $X^b$ are not cyano, then $A^a$ and $A^b$ are bonded to each other to form a ring selected from the following structures, wherein "*", $R_0$ and $R_1$ have the same meanings as above:

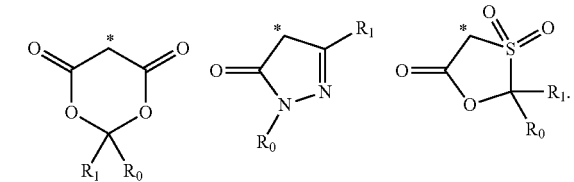

4. A polymer film comprising at least one compound represented by formula (V) or (VII):

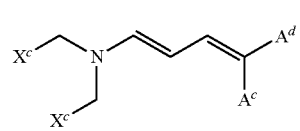
(V)

wherein $X^c$ represents cyano or an alkyl-oxycarbonyl; and when $X^c$ represents cyano, then $A^c$ and $A^d$ each independently represents an alkyl- or aryl-carbonyl group, alkyl-oxycarbonyl group or cyano, or bond to each other to form one selected from Active Methylene Group (II):

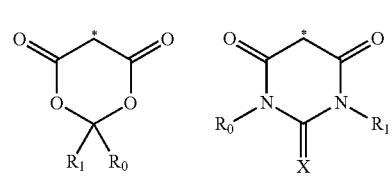
(II)

-continued

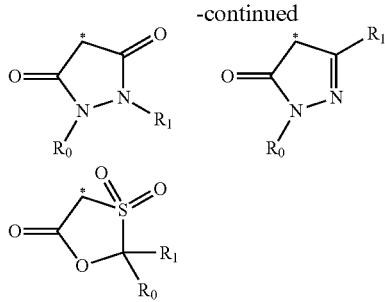

where, in formulas, "*" indicates a portion linking to formula (I); $R_0$ and $R_1$ each independently represents a hydrogen atom or an alkyl or phenyl group which may have at least one substituent, or bond to each other to form a ring; and X represents an oxygen or sulfur atom, and when $X^c$ represents an alkyl-oxycarbonyl, then $A^c$ and $A^d$ are bonded to each other to form a ring selected from the following structures:

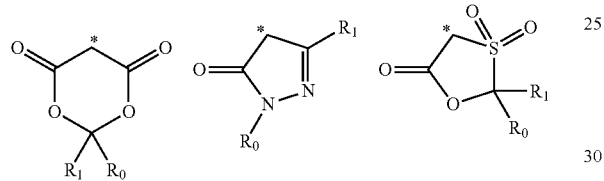

where "*" indicates a portion linking to formula (V); and $R_0$ and $R_1$ each independently represents a hydrogen atom or an alkyl or phenyl group which may have at least one substituent, or bond to each other to form a ring; and

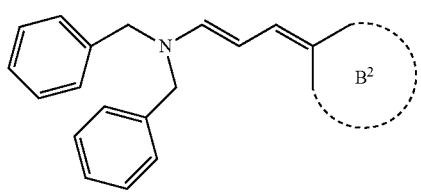
(VII)

where, in formula (VII), $B^2$ represents one selected from the following structures:

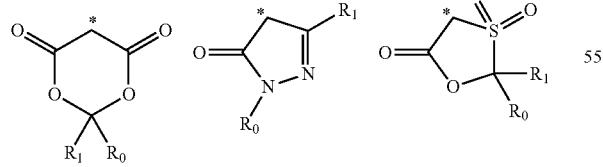

where "*" indicates a portion linking to formula (VII); and $R_0$ and $R_1$ each independently represents a hydrogen atom or an alkyl or phenyl group which may have at least one substituent, or bond to each other to form a ring.

5. An ultraviolet absorber comprising at least one compound represented by formula (V) or (VII):

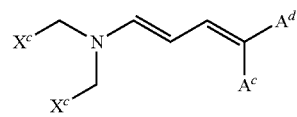
(V)

wherein $X^c$ represents cyano or an alkyl-oxycarbonyl; and when $X^c$ represents cyano, then $A^c$ and $A^d$ each independently represents an alkyl- or aryl-carbonyl group, alkyl-oxycarbonyl group or cyano, or bond to each other to form one selected from Active Methylene Group (II):

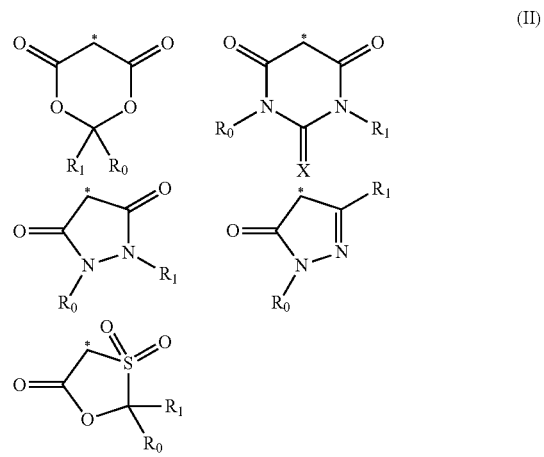
(II)

where, in formulas, "*" indicates a portion linking to formula (I); $R_0$ and $R_1$ each independently represents a hydrogen atom or an alkyl or phenyl group which may have at least one substituent, or bond each other to form a ring; and X represents an oxygen or sulfur atom, and when $X^c$ represents an alkyl-oxycarbonyl, then $A^c$ and $A^d$ are bonded to each other to form a ring selected from the following structures:

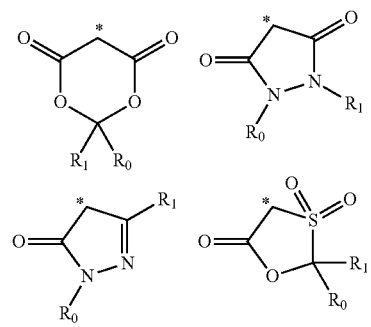

where "*" indicates a portion linking to formula (V); and $R_0$ and $R_1$ each independently represents a hydrogen atom or an alkyl or phenyl group which may have at least one substituent, or bond to each other to form a ring; and:

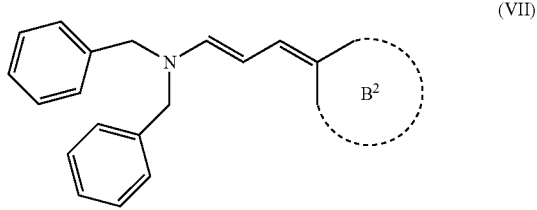 [SMILES: CC(C)=C/C=C/N(Cc1ccccc1)Cc1ccccc1]

(VII)

where, in formula (VII), $B^2$ represents one selected from the following structures:

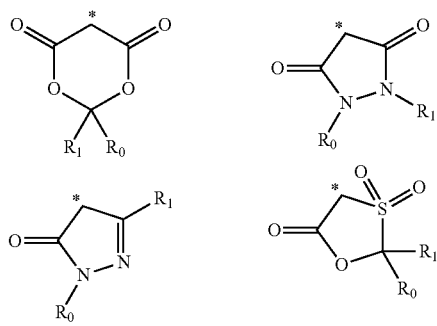

where "*" indicates a portion linking to formula (VII); and $R_0$ and $R_1$ each independently represents a hydrogen atom or an alkyl or phenyl group which may have at least one substituent, or bond to each other to form a ring.

6. A merocyanine compound represented by formula (V):

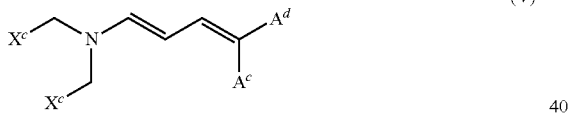

(V)

wherein $X^c$ represents cyano or an alkyl-oxycarbonyl; and when $X^c$ represents cyano, then $A^c$ and $A^d$ each independently represents an alkyl- or aryl-carbonyl group, alkyl-oxycarbonyl group or cyano, or bond to each other to form one selected from Active Methylene Group (II):

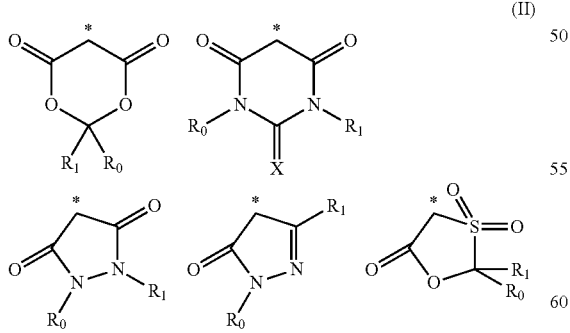

(II)

where, in formulas, "*" indicates a portion linking to formula (I); $R_0$ and $R_1$ each independently represents a hydrogen atom or an alkyl or phenyl group which may have at least one substituent, or bond to each other to form a ring; and X represents an oxygen or sulfur atom, and when $X^c$ represents an alkyl-oxycarbonyl, then $A^c$ and $A^d$ are bonded to each other to form a ring selected from the following structures:

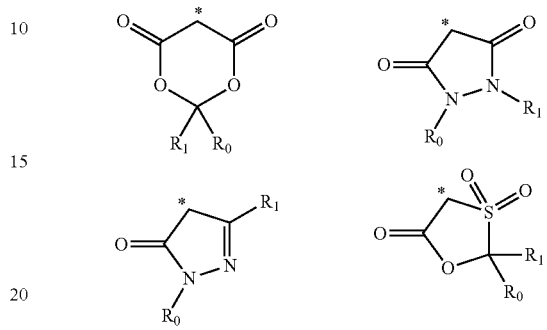

where "*" indicates a portion linking to formula (V); and $R_0$ and $R_1$ each independently represents a hydrogen atom or an alkyl or phenyl group which may have at least one substituent, or bond to each other to form a ring.

7. A merocyanine compound represented by formula (VI):

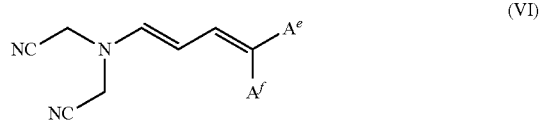

(VI)

wherein $A^e$ and $A^f$ each independently represents an alkyl- or aryl-carbonyl group, alkyl-oxycarbonyl group, or cyano, or bond to each other to form a ring selected from Active Methylene Group (II):

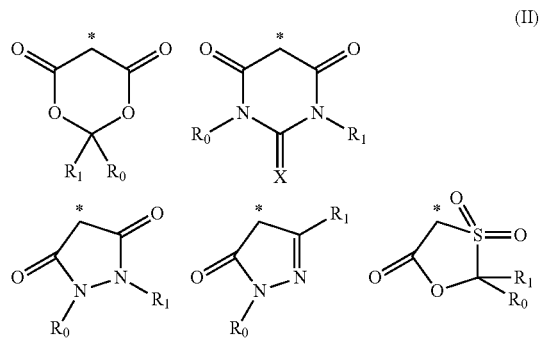

(II)

where, in formulas, "*" indicates a portion linking to formula (VI); $R_0$ and $R_1$ each independently represents a hydrogen atom or an alkyl or phenyl group which may have at least one substituent, or bond to each other to form a ring; and X represents an oxygen or sulfur atom.

* * * * *